United States Patent [19]

Mildenberger et al.

[11] Patent Number: 5,013,444

[45] Date of Patent: May 7, 1991

[54] PROCESS FOR SEPARATING OFF ENOL ETHERS FROM REACTION MIXTURES CONTAINING ALCOHOLS

[75] Inventors: Hilmar Mildenberger, Kelkheim/Taunus; Stephen Lachhein, Hofheim am Taunus; Siegbert Rittner, Mörfelden; Heribert Tetzlaff, Frankfurt am Main, all of Fed. Rep. of Germany

[73] Assignee: Hoechst Aktiengesellschaft, Frankfurt am Main, Fed. Rep. of Germany

[21] Appl. No.: 576,934

[22] Filed: Aug. 29, 1990

[30] Foreign Application Priority Data

Aug. 31, 1989 [DE] Fed. Rep. of Germany ....... 3928774

[51] Int. Cl.$^5$ .................. B01D 11/04; C02F 1/26; C02F 1/44
[52] U.S. Cl. ..................... 210/634; 203/43; 210/767; 210/781; 568/693; 568/699
[58] Field of Search .............. 210/634, 639, 908, 909, 210/767, 781; 203/43; 568/693, 699

[56] References Cited

U.S. PATENT DOCUMENTS

| 493,420 | 10/1938 | Aktiengesllschaft | 210/634 |
| 1,314,124 | 4/1973 | Shionogi | 210/634 |
| 2,476,206 | 7/1949 | McCants | 203/43 |
| 4,857,664 | 8/1989 | Huang et al. | 568/699 |

FOREIGN PATENT DOCUMENTS

| 2056970 | 3/1981 | United Kingdom | 568/699 |

*Primary Examiner*—Robert A. Dawson
*Assistant Examiner*—Ana M. Fortuna
*Attorney, Agent, or Firm*—Curtis, Morris & Safford

[57] ABSTRACT

The invention relates to a gentle process for the separation of enol ethers from mixtures containing water-soluble alcohols by extraction, wherein an aqueous solution of a base is used as the extraction agent in a phase ratio of the amounts of the aqueous phase: enol ether/alcohol mixture of at least 0.5:1 and the extraction is carried out in several stages or continuously with a theoretical number of stages of at least two. The process is particularly suitable for separating off enol ethers which readily decompose during distillation.

17 Claims, No Drawings

PROCESS FOR SEPARATING OFF ENOL ETHERS FROM REACTION MIXTURES CONTAINING ALCOHOLS

Enol ethers are important intermediates in the synthesis of cyclic and heterocyclic compounds (for example plant protection agents) or also for the preparation of allylphenols (by Claisen rearrangement from allyl phenyl ethers). When prepared from ketones and, for example, methanol, they are obtained as a mixture with methanol. Separating off enol ethers from a methanolic solution by distillation or rectification under reduced pressure is described, for example, in Japanese Patent A-75/96512 and J. Org. Chem. 40 (1981), page 2532 et seq.

If methanol and enol ethers form an azeotrope, in some cases it is possible to employ extractive distillation in which a high-boiling third component which is added remains in the bottom of the column together with one of the two substances (German Patent C-2,305,021 and L. Berg, A. Yeh in AIChE Journal 31 (1985), page 504 et seq.). The distillation processes have the disadvantage that sensitive enol ethers are partly or completely destroyed in these processes.

It is known that in some cases of purification of methanol/enol ether mixtures by distillation in the laboratory, some of the methanol can be removed by washing with dilute KOH solution before the distillation (J. Chem. Thermodynamics 5 (1973), 783 et seq.). However, the separation by distillation which is still necessary in the known process continues to be a disadvantage for the abovementioned reasons.

The object was therefore to provide a process for the separation of enol ether/alcohol mixtures which is suitable for sensitive enol ethers and can also be carried out on a large industrial scale.

The invention relates to a process for the separation of enol ethers and water-soluble alcohols by extraction, which comprises using as the extraction agent an aqueous solution of a base in a phase ratio of the amounts of aqueous phase:enol ether/alcohol mixture of at least 0.5:1, preferably at least 1:1 and in particular 1.4:1 to 1.7:1, based on the weights of the phases, and carrying out the reaction in several stages or continuously with a theoretical number of stages of at least 2.

Suitable enol ethers are all the essentially water-insoluble enol ethers which are liquid below the critical temperature of the enol ether-alcohol-water system (disappearance of the miscibility gap).

Enol ethers which are preferably suitable are those from the group comprising 2-($C_1$–$C_4$-alkoxy)-$C_3$–$C_{16}$-alk-1-enes, such as 2-methoxy-, 2-ethoxy-, 2-propoxy-, 2-isopropoxy-, 2-n-butoxy-, 2-isobutoxy-, 2-t-butoxy- and 2-sec-butoxyalkenes, in particular 2-methoxy-3-methyl-1-butene.

Suitable water-soluble alcohols are above all methanol, ethanol, propanol, isopropanol, n-butanol and isobutanol, but in particular methanol. Enol ether/alcohol mixtures such as are formed in the preparation of enol ethers from the corresponding ketals by splitting of alcohol and subsequent working up, in particular azeotropic mixtures of enol ether and alcohol, are preferably employed for the separation.

Aqueous solutions of inorganic and/or organic bases are advantageously employed as extraction agents for the process according to the invention. The solutions as a rule have a pH of between 7 and 14. Dilute, weakly basic solutions having a pH of between 7 and 12 are preferred. The normalities here are as a rule in the range from $10^{-4}$ to 1N, preferably $10^{-4}$ to $10^{-1}$N base solution.

Suitable basic extraction agents are dilute solutions of alkali metal hydroxides, such as NaOH and KOH, soluble carbonates, such as alkali metal carbonates (for example $Na_2CO_3$ and $K_2CO_3$) or $(NH_4)_2CO_3$, and alkaline earth metal hydroxides, such as $Ba(OH)_2$ and $Ca(OH)_2$. Solutions of organic bases, such as amines, for example tertiary amines, such as triethylamine, trimethylamine or ethyl dimethylamine, are likewise suitable. 0.0005 to 1N, in particular 0.0005 to 0.002N NaOH or KOH solutions and 0.005 to 1N, in particular 0.0005 to 0.02 normal aqueous solutions of $Na_2CO_3$, $K_2CO_3$ or triethylamine are preferred.

The process according to the invention is carried out, for example, by intimately mixing the enol ether/alcohol mixture to be separated with the suitable amount of extraction agent and then leaving the mixture to stand until the phases have separated. When the phases have been separated off with the aid of customary devices, the procedure is repeated with the enol ether phase once or several times until the desired purity is reached. In order to avoid losses of enol ether via the aqueous phase, the multistage extraction is preferably carried out by the countercurrent principle. The multistage process can be carried out discontinuously, semicontinuously or continuously. Purities of more than 99.8% by weight in the enol ether phase can already be achieved after two separation operations, depending on the particular enol ether, the ratio of the amounts of the phases and the temperature. For practical reasons, the temperature is preferably 10° to 30° C., in particular room temperature, but can in principle lie between the melting point of the mixture and the critical point (disappearance of the miscibility gap), the separation as a rule being somewhat better at lower temperatures.

The quality of the separation is shown by the partition coefficients $K_D$, defined here as the ratio of the concentration of a substance in the enol ether phase to its concentration in the aqueous phase. The separation effort required for separating the enol ether/alcohol mixtures is characterized by the separation factor $\beta = K_D$(enol ether)/$K_D$(alcohol). It is a measure of the number of stages required and the ratio of the amounts of phases when realizing an extraction/separation process.

The separation of enol ether/alcohol mixtures by extraction is most economically carried out by multistage continuous countercurrent partition. All the customary extraction apparatuses are suitable as the apparatuses for carrying out the extraction (for example columns, mixer-settlers, a Graesser extractor or a centrifugal extractor).

A further advantage of the gentle extraction/separation process according to the invention lies in the fact that the degree of separating off of the alcohol from the enol ether phase can be selected as high as required via the number of stages. The weakly basic aqueous solution moreover prevents decomposition of the enol ether to form the ketal.

Small residues (less than 0.5% by weight) of enol ether which emerge from the extraction together with the aqueous-alcoholic raffinate phase can be separated off from this by distillation as an alcohol/enol ether azeotrope and recycled into the extraction stage of the process.

During the working up by distillation, in addition to the alcohol/enol ether azeotrope, most of the extracted alcohol can furthermore be separated off from the aqueous phase, in which case the aqueous phase purified in this way can be recycled into the circulation, i.e. can be reused as extraction agent for the process according to the invention. By working up of the aqueous-alcoholic phase by distillation, recycling of the enol ether/alcohol azeotrope and recycling of the aqueous basic phase, the process produces only the now separated components of enol ether and alcohol contained in the starting mixture, it being possible for the degree of purity of the enol ether to be increased as required by means of a multi-stage procedure by the countercurrent principle. Working up of the aqueous-alcoholic phase by distillation for the recycling of the enol ether residues is suitable above all when methanol is the alcohol. In the case of other water-soluble alcohols, the azeotrope formation of water/alcohol sometimes makes working up of the aqueous-alcoholic raffinate by distillation and therefore re-use in the circulation (recycling) of the aqueous phase more difficult. In the case of alcohols having boiling points above 100° C. here, salt-like bases should be avoided in the preparation of the basic medium in the aqueous phase, since these may be deposited in the alcohol phase during working up of the raffinate by distillation. Liquid organic bases are more suitable in such cases.

The process is illustrated in more detail in the following Examples 1 to 4, without it being intended to limit the possible process conditions to the examples shown.

1. Separation of a mixture of 2-methoxy-3-methyl-1-butene (51.07% by weight) and methanol (48.93% by weight):

A mixture of 51.07% by weight of 2-methoxy-3-methyl-1-butene (I) and 48.93% by weight of methanol is separated into an enol ether phase containing 99.83% by weight of (I), not more than 0.02% by weight of methanol and 0.15% by weight of water and into an aqueous phase containing 25.18% by weight of methanol and 0.41% by weight of (I) by three-stage batchwise countercurrent extraction in accordance with the Watanabe and Morikawa model (see Houben Weyl, Meth. d. org. Chemie, 4. Aufl. (1958) G. Thieme Verlag, Stuttgart, Bd. I/1, pages 255 ff.) at room temperature and at a phase ratio of the amounts of enol ether/methanol mixture to 0.001N NaOH of 1:1.45. The breakdown of the amounts is shown in Table 1 (see page 7).

2. A mixture as described in Example 1 is employed. A mixture of 57.8% by weight of (I) and 42.2% by weight of methanol is separated into an enol ether phase containing 99.91% by weight of (I), not more than 0.01% by weight of methanol and 0.08% by weight of water and into an aqueous phase containing 19.7% by weight of methanol and 0.39% by weight of (I) by four-stage continuous countercurrent extraction in a laboratory mixer-settler battery at room temperature and at a phase ratio of the amounts of enol ether/methanol mixture to 0.01N $Na_2CO_3$ solution of 1:1.7.

3. A mixture as described in Example 1 is employed. A mixture of 52.3% by weight of (I) and 47.7% by weight of methanol is separated into an enol ether phase containing 99.89% by weight of (I), 0.02% by weight of methanol and 0.09% by weight of water and into an aqueous phase containing 24.0% by weight of methanol and 0.45% by weight of (I) by continuous countercurrent extraction in a laboratory Karr column (oscillating tray column of diameter 25 mm and height 2 m, number of theoretical stages 5) at room temperature and at a phase ratio of the amounts of enol ether/methanol mixture to 0.01N aqueous triethylamine solution of 1:1.5. In this procedure, some of the triethylamine passes into the enol ether phase and additionally stabilizes the enol ether from decomposition.

4. A mixture of 81.5% by weight of enol ether and 18.5% by weight of methanol is employed (10 kg/h).

TABLE 1

3-Stage countercurrent extraction of an enol ether/methanol mixture (S) with 0.001 N NaOH solution (X) at room temperature. The extraction is carried out batchwise in accordance with the Watanabe-Morikawa model, which produces the same results as a continuous countercurrent extraction at 100% stage efficiency. Ratio of the amounts of phase: S:X = 1:1.45.

|  | Amount g | Enol ether (% by weight) | Methanol (% by weight) | Water (% by weight) |
|---|---|---|---|---|
| Feed solution (S) | 136.88 | 51.07 | 48.93 | — |
| 0.001 N NaOH | 197.99 | — | — | about 100 |
| Enol ether phase | 68.93 | 99.83 | ≦0.02 | 0.15 |
| Aqueous phase | 265.94 | 0.41 | 25.18 | 74.41 |

An enol ether extract which has a purity of more than 99.93% by weight and contains less than 0.07% by weight of methanol is obtained by continuous countercurrent extraction in a four-stage centrifugal extractor (type LX 124, Robatel, speed of rotation 2,900 min$^{-1}$) using 0.01N sodium hydroxide solution (10 kg/h).

COMPARISON EXAMPLES A, B, C

The efficiency of the extraction/separation process for splitting up enol ether/methanol mixtures is illustrated with the aid of the partition coefficients and separation factors. For this, in each case a certain amount of an approximately half-and-half mixture of 2-methoxy-3-methyl-1-butene and methanol is brought into equilibrium with the extraction agent (0.001N NaOH) by intensive mixing at room temperature. The phases are then allowed to settle and are separated and the concentrations of the constituents in the two phases are determined. The experimental results of the comparison examples are summarized in Table 2.

Comparison Examples A, B and C show that, in a one-stage procedure, adequate separation of the alcohol from the enol ether phase is not possible even if the phase ratio of the aqueous phase:enol ether/alcohol mixture is greatly increased.

TABLE 2

Breakdown of the amounts, partition coefficients $K_D$ (= concentration of a substance in the enol ether phase/concentration of this substance in the aqueous phase) and separation factors $\beta$ (= $K_D$ (enol ether)/$K_D$ (methanol)) for the splitting up of enol ether/methanol mixtures using 0.001 N NaOH; S = feed solution (mixture employed)

|  | Amount g | Enol ether (% by wt.) | Methanol (% by wt.) | Water (% by wt.) | $K_D$ (enol ether) | $K_D$ methanol) | $K_D$ (water) | $\beta$ |
|---|---|---|---|---|---|---|---|---|
| (A) |  |  |  |  |  |  |  |  |
| Amount weighed out of S | 39.80 | 50.00 | 50.00 | — |  |  |  |  |

TABLE 2-continued

Breakdown of the amounts, partition coefficients $K_D$ (= concentration of a substance in the enol ether phase/concentration of this substance in the aqueous phase) and separation factors $\beta$ (= $K_D$(enol ether)/$K_D$(methanol)) for the splitting up of enol ether/methanol mixtures using 0.001 N NaOH; S = feed solution (mixture employed)

| | Amount g | Enol ether (% by wt.) | Methanol (% by wt.) | Water (% by wt.) | $K_D$ (enol ether) | $K_D$ methanol | $K_D$ (water) | $\beta$ |
|---|---|---|---|---|---|---|---|---|
| Amount weighed out of 0.001 N NaOH | 49.83 | — | — | about 100 | | | | |
| Enol ether phase | 19.76 | 99.14 | 0.63 | 0.23 | | | | |
| Aqueous phase | 69.87 | 0.44 | 28.30 | 71.26 | 230 | 0.022 | 0.0032 | 10,000 |
| (B) | | | | | | | | |
| Amount weighed out of S | 19.74 | 50.00 | 50.00 | — | | | | |
| Amount weighed out of 0.001 N NaOH | 49.80 | — | — | about 100 | | | | |
| Enol ether phase | 9.78 | 99.54 | 0.28 | 0.18 | | | | |
| Aqueous phase | 59.76 | 0.23 | 16.47 | 83.30 | 430 | 0.017 | 0.0022 | 25,000 |
| (C) | | | | | | | | |
| Amount weighed out of S | 15.75 | 50.00 | 50.00 | — | | | | |
| Amount weighed out of 0.001 N NaOH | 79.50 | — | — | about 100 | | | | |
| Enol ether phase | 7.77 | 99.72 | 0.14 | 0.14 | | | | |
| Aqueous phase | 87.48 | 0.15 | 8.99 | 90.86 | 660 | 0.016 | 0.0115 | 41,000 |

We claim:

1. A process for the separation of enol ethers and water-soluble alcohols by extraction, which comprises using as the extraction agent an aqueous solution of a base in a phase ratio of the amount of aqueous phase:enol ether/alcohol mixture of at least 0.5:1; based on the weights of the phases, and carrying out the reaction in several stages or continuously with a theoretical number of stages of at least 2.

2. The process as claimed in claim 1, wherein a mixture of a 2-($C_1$–$C_4$-alkoxy)-$C_3$–$C_9$-alk-1-ene and a $C_1$–$C_4$-alcohol is employed.

3. The process as claimed in of claim 1, wherein an azeotropic mixture of enol ether and alcohol is employed.

4. The process as claimed in claim 1, wherein the phase ratio of the amounts of aqueous phase:enol ether/alcohol mixture is from 1.4:1 to 1.7:1.

5. The process as claimed in claim 1, wherein a dilute aqueous solution of NaOH, KOH, Ba(OH)$_2$, Ca(OH)$_2$ or an amine is employed as the aqueous solution.

6. The process as claimed in claim 1, wherein the pH in the aqueous phase is between 7 and 14.

7. The process as claimed in claim 1, wherein the extraction is carried out in several stages by the countercurrent principle.

8. The process as claimed in claim 1, wherein the temperature is 10° to 30° C.

9. The process as claimed in claim 1, wherein the aqueous-alcoholic raffinate phase which occurs after the extraction is worked up by distillation and the residues of enol ether separated off here as an alcohol/enol azeotrope and the aqueous phase freed from most of the alcohol are recycled into the extraction.

10. The process as claimed in claim 1, wherein the water-soluble alcohol is methanol.

11. The process as claimed in claim 2, wherein the phase ratio of the amounts of aqueous phase:enol ether/alcohol mixture is from 1.4:1.

12. The process as claimed in claim 11, wherein a dilute aqueous solution of NaOH, KOH, Ba(OH)$_2$, Ca(OH)$_2$ or an amine is employed as the aqueous solution.

13. The process as claimed in claim 12, wherein the pH in the aqueous phase is between 7 and 14.

14. The process as claimed in claim 13, wherein the extraction is carried out in several stages by the countercurrent principle.

15. The process as claimed in claim 14, wherein the temperature is 10° to 30° C.

16. The process as claimed in claim 15, wherein the water-soluble alcohol is methanol.

17. The process as claimed in claim 2, wherein the water-soluble alcohol is methanol.

* * * * *